United States Patent [19]  [11] Patent Number: 4,835,242
Eggersdorfer et al.  [45] Date of Patent: May 30, 1989

[54] ARYL ETHER KETONES

[75] Inventors: Manfred Eggersdorfer, Frankenthal; Jochem Henkelmann, Mutterstadt; Gerhard Heinz, Weisenheim; Juergen Koch, Neuhofen, all of Fed. Rep. of Germany

[73] Assignee: Basf Aktiengesellschaft, Ludwigshafen, Fed. Rep. of Germany

[21] Appl. No.: 142,798

[22] Filed: Jan. 11, 1988

[30] Foreign Application Priority Data

Jan. 14, 1987 [DE] Fed. Rep. of Germany ....... 3700809

[51] Int. Cl.$^4$ .................. C08G 8/02; C08G 14/00
[52] U.S. Cl. .................... 528/125; 528/126; 528/128; 528/174; 528/175
[58] Field of Search ............ 528/125, 126, 128, 174, 528/175

[56] References Cited
U.S. PATENT DOCUMENTS 4,616,056 10/1986 Chan et al. ..................... 528/125

FOREIGN PATENT DOCUMENTS 1879 3/1982 European Pat. Off. .

Primary Examiner—John Kight
Assistant Examiner—M. L. Moore
Attorney, Agent, or Firm—John H. Shurtleff

[57] ABSTRACT

Aryl ether ketones of the general formula I

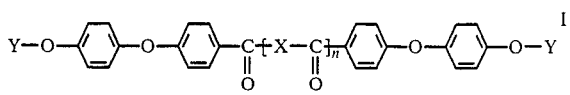

where
n is from 0 to 5,
X is and
Y is tert-butyl, acetyl, benzyl, benzoyl, tert-butoxycarbonyl or, in the case of n=0, H,
and the ring-substituted $C_1$–$C_8$-alkyl, $C_1$–$C_8$-alkoxy, aryl, chlorine or fluorine derivatives thereof are useful for preparing highly heat-resistant polyaryl ether ketones.

7 Claims, No Drawings

ARYL ETHER KETONES

The present invention relates to novel aryl ether ketones of the general formula I

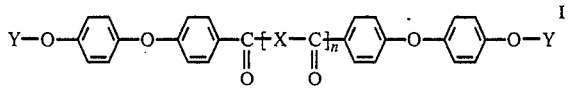

where
n is from 0 to 5,
X is

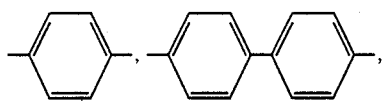

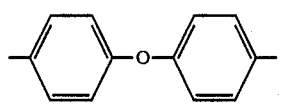

and
Y is tert-butyl, acetyl, benzyl, benzoyl, tert-butoxycarbonyl or, in the case of n=O, H,
and to ring-substituted $C_1$-$C_8$-alkyl, $C_1$-$C_8$-alkoxy, aryl, chlorine and fluorine derivatives thereof.

The present invention further relates to a method of using the above-defined compound I as a monomer for preparing highly heat-resistant polyaryl ether ketones composed of (A) from 50 to 100 mol % of repeat units of the general formula IV

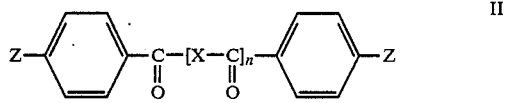

or ring-substituted $C_1$-$C_8$-alkyl, $C_1$-$C_8$-alkoxy, aryl, chlorine or fluorine derivatives thereof and (B) from 0 to 50 mol % of repeat units, different from IV, of the general formulae V and/or VI

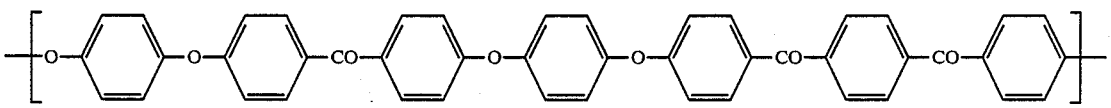

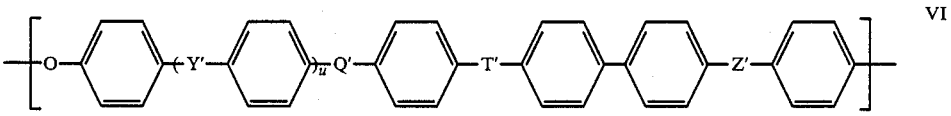

or ring-substituted $C_1$-$C_8$-alkyl, $C_1$-$C_8$-alkoxy, aryl, chlorine or fluorine derivatives thereof, where Q, Q', Y, Y', T, T', Z and Z' can each be —O—, —CO— or a chemical bond, one or more of these substituents is a —CO— group, and s, t and u are each 0 or 1.

EP-A-1,879 discloses polyaryl ether ketones having repeat units of the formula

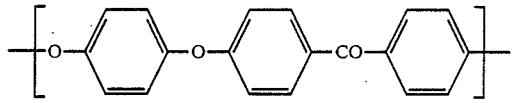

which may contain up to 50 mol % of other polyaryl ether ketone units. However, these products are not sufficiently heat-resistant for some applications. In addition, the 4,4'-difluorobenzophenone used as a monomer in said EP-A is very expensive.

It is an object of the present invention to provide a simply and inexpensively accessible monomer from which polyaryl ether ketones of high heat distortion resistance can be prepared.

We have found that this object is achieved with the aryl ether ketone of the formula I defined at the beginning. In principle, the aromatic units therein can be substituted by $C_1$-$C_8$-alkyl, $C_1$-$C_8$-alkoxy, aryl, chlorine or fluorine. Examples of substituents of this type are methyl, ethyl, i-propyl, n-, i- or t-butyl, the corresponding alkoxy groups and also phenoxy groups. In generaly, however, the unsubstituted derivatives are preferred.

The aryl ether ketone I is advantageously prepared by reacting an aromatic ketone of the general formula II

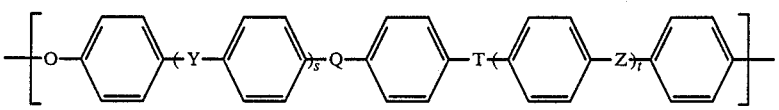

where Z is a nucleophilic leaving group, for example fluorine, bromine, chlorine, tosyl (p-toluenesulfonyl) or mesyl (methanesulfonyl), with a hydroquinone derivative of the general formula III

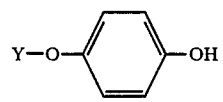

where Y is one of the alcohol protective groups mentioned in claim 1, in the presence of a base, for example an alkali metal or alkaline earth metal carbonate, hydroxide or alcoholate, such as sodium carbonate, potassium carbonate, sodium hydroxide, sodium ethylate, potassium hydroxide or potassium methylate, or alkali metal amides or hydrides such as sodium amide, sodium hydride, potassium amide or potassium hydride, in a diluent. To prepare the hydroxylated compound (Y=H) the alcohol protective groups can be cleaved in a conventional manner for example by treatment with an acid, eg. a mineral acid such as hydrochloric acid.

The basic path of the synthesis may be illustrated by reference to the preparation of 1,4-bis(p-hydroxyphenoxybenzoyl)benzene starting from p-tert-butoxyphenol and 1,4-di(4-chlorobenzoyl)benzene:

benzene or 4,4'-di[4-(4-hydroxyphenoxy)benzoyl]benzene and 4,4'-difluorobenzophenone can be used as monomers.

The process conditions for preparing the polyaryl ether ketone, such as temperature, pressure, type of solvent and type of additives (catalysts) if any, are the same as described in EP-A-1,879, so that no details are required here.

It is particularly convenient to carry out the reaction in an aprotic polar solvent in the presence of an anhydrous alkali metal carbonate as base. A particularly preferred combination consists of diphenyl sulfone as

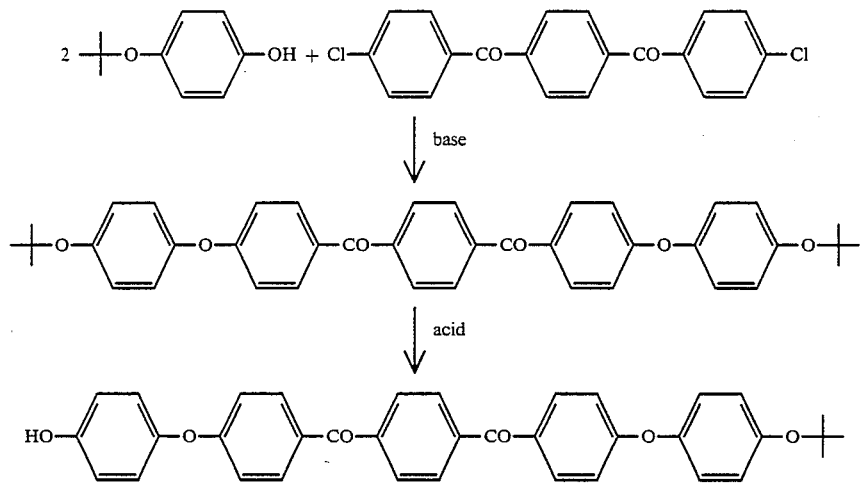

The starting materials II and III are commonly known and easily accessible in a conventional manner.

The reaction is carried out in a conventional manner, so that some general remarks should be sufficient here. For instance, advantageously it is possible to use 2 moles of the hydroquinone derivative III and from 0.2 to 2.5 moles of the base per mole of aromatic ketone II. The reaction is carried out in the presence of an inert organic solvent or diluent. Suitable in particular are aprotic solvents, eg. N-methylpyrrolidone, sulfolane, dimethylpropyleneureas, dimethylethyleneurea, tetrabutylurea and hexamethylphosphoramide. The reaction temperature can be varied within wide limits, and in general ranges from 80° to 220° C., in particular from 140° to 190° C.

In the products thus obtained, the alcohol functions can be freed in a conventional manner, for example as described by A. Streitwieser, Jr., and C. H. Heathcook in Introduction to Organic Chemistry, p. 216, MacMillan Publishing Company, New York, so that no details are required here.

By the sequence of reactions described and subsequent purification, for example by crystallization, the hydroxylated aryl ether ketones (Y=H) can be obtained in good yields and high purity. They are highly suitable for use as monomers for polymerizations and polycondensations. Preferably, they can be used for preparing polyaryl ether ketones as defined at the beginning.

Polyaryl ether ketones of this type can be prepared by a conventional nucleophilic or electrophilic process.

A first possible method of preparation comprises polycondensing dihydroxy compounds with dihalo compounds, which is common knowledge.

In the present case, for example, 4,4'-di(4-hydroxyphenoxy)benzophenone and 1,4-di(4-fluorobenzoyl)- solvent and K$_2$CO$_3$ as base.

The amount of diphenyl sulfone ranges in general from 5 to 100 moles, preferably from 5 to 20 moles, per mole of monomer. This produces a preferred solids content of the reaction solution within the range from 5 to 50% by weight, particularly preferably from 10 to 40% by weight.

The water formed in the course of the polycondensation can be removed by means of an azeotropic agent, by employing reduced pressure or preferably by introducing a nitrogen stream and distilling off.

Suitable azeotropic agents are all those compounds which, under atmospheric pressure, boil within the range of the reaction temperature and are homogeneously miscible with the reaction mixture without entering into chemical reactions.

The reaction temperature is generally within the range from 150° to 400° C., preferably 250° to 400° C., and in particular 250° to 350° C.; the total reaction time depends on the desired degree of condensation, but in general is within the range from 0.1 to 15 hours.

After the polycondensation, the product can be stabilized by reacting free phenolate end groups with an arylating or alkylating agent, eg. methyl chloride. This is preferably done at up to 350° C., the lower temperature limit being determined by the solubility of the polymer in the solvent used.

The reaction product can be worked up in a conventional manner. Advantageously, the melt is turned into a finely divided material which is freed from solvent (eg. diphenyl sulfone) by extraction with a suitable solvent, eg. acetone. Thereafter, residues of alkali metal carbonate and alkali metal fluorine can be removed by extraction with water.

The conditions for a preparation in an electrophilic manner, viz. a method of preparation by Friedel-Crafts acylation, are described for example in EP-A-124,276 or EP-A-138,990 and U.S. Pat. No. 3,956,240.

In the polyaryl ether ketones of the formula IV, units of the formulae V and/or VI which can be prepared by basically the same process conditions as described above for the preparation of polyaryl ether ketones having repeat units of the formula IV can be present in random distribution or in the form of blocks.

A detailed description of these polyaryl ether ketones can be found in German Application No. P 37 00 810.2 (O.Z. 0050/38907) of the same date.

EXAMPLES 1 TO 5

Preparation of monomeric aryl ether ketones

Example 1

4,4′-Di(tert-butoxyphenoxy)benzophenone

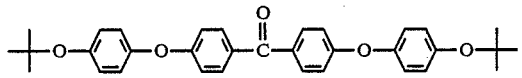

176 g (1.06 mol) of p-tert-butoxyphenol were reacted with 143 g (0.5 mol) of 4,4′-dichlorobenzophenone and 76 g of potassium carbonate in 250 ml of N-methylpyrrolidone at 180°–190° C. in the course of 1 h. After cooling down, 100 ml of H$_2$O were added with thorough stirring to the reaction batch. The precipitated solid was filtered off with suction and recrystallized from methanol. Yield: 169 g ($\doteq$85% of theory) of colorless crystals. Melting point: 182° C.

Example 2

1,4-Di(p-tert-butoxyphenoxybenzoyl)benzene

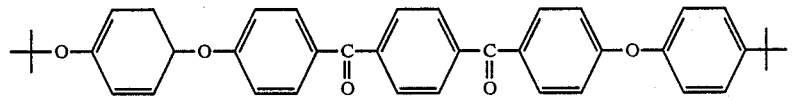

By the method of Example 1, 166 g (1 mol) of p-tert-butoxyphenol were reacted with 195 g (0.5 mol) of di(4-chlorobenzoyl)benzene in 250 ml of N,N′-dimethylethyleneurea and 76 g of potassium carbonate and worked up. Yield: 295 g (=96% of theory) of colorless crystals. Melting point: 221° C.

Example 3

1,4-Di(p-hydroxyphenoxybenzoyl)benzene

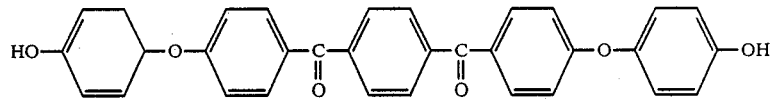

100 ml of concentrated HCl solution were slowly added dropwise at room temperature to a suspension of 153.5 g (0.25 mol) of 1,4-di(p-tert-butoxyphenoxybenzoyl)benzene in 200 ml of H$_2$O. This was followed by 2 hours of stirring at 60° C. After cooling down, the solid was filtered off with suction, recrystallized from methanol and dried.

Yield: 119 g ($\doteq$95% of theory) of colorless crystals.
Melting point: 236° C.

EXAMPLE 4

4,4′-Di(p-tert-butoxyphenoxybenzoyl)diphenyl

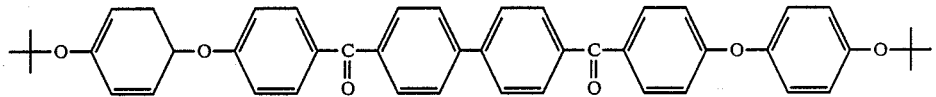

By the method of Example 1, 166 g (1 mol) of p-tert-butoxyphenol were reacted with 199 g (0.5 mol) of 4,4′-di(4-fluorobenzoyl)diphenyl in 250 ml of N-methylpyrrolidone and 76 g of potassium carbonate and worked up.

Yield: 317 g ($\doteq$92% of theory) of colorless crystals.
Melting point: 225° C.

Example 5

4,4′-Di(p-hydroxyphenoxybenzoyl)diphenyl

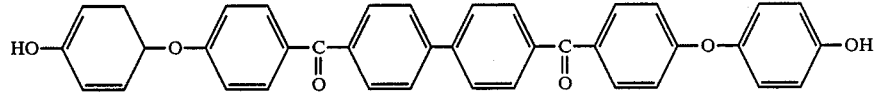

By the method of Example 3, 172.5 g (0.25 mol) of 4,4′-di(p-tert-butoxyphenoxybenzoyl)diphenyl were reacted in 200 ml of H$_2$O with 100 ml of concentrated HCl solution and worked up.

Yield: 136 g ($\doteq$94% of theory) of colorless crystals.
Melting point: 241° C.

EXAMPLES 6 AND 7

Preparation of polyaryl ether ketones

Example 6

In a four-necked glass flask equipped with a stirrer, a nitrogen inlet, an internal thermometer and an air cooler, 79.68 g (0.2 mol) of 4,4′-di(4-hydroxyphenoxy)benzophenone, 64.46 g (0.2 mol) of bis(4-fluorobenzoyl)benzene, 30.41 g (0.22 mol) of potassium carbonate and 800 g of diphenyl sulfone were heated to 200° C.

and maintained at that temperature for 2 hours. The temperature was then raised to 240° C., maintained for 1 hour, then to 280° C., maintained for 1 hour, then to 320° C. and again maintained for 1 hour. After cooling down, the reaction mass was ground. The resulting fine powder was washed four times for 10 minutes with hot acetone, three times for 10 minutes with boiling water and for a further 5 minutes with acetone to remove diphenyl sulfone and inorganic matter. The polymer powder thus obtained was dried at 150° C. under reduced pressure for 10 hours. According to DSC, the polymer had a glass transition point of 151° C. and a melting point of 352° C. The reduced viscosity was 1.41 (measured in concentrated sulfuric acid).

A larger amount of polymer prepared in the same way was satisfactorily extrudable at 400° C. without change in the molecular weight.

EXAMPLE 7

100.50 g (0.2 mol) of 1,4-di[4-(4-hydroxyphenoxy)-benzoyl]benzene, 43.64 g (0.2 mol) of 4,4'-difluorobenzophenone and 30.41 g (0.22 mol) of potassium carbonate were reacted in 800 g of diphenyl sulfone under the same conditions as in Example 6.

The polymer thus obtained had a reduced viscosity of 1.38 (measured in concentrated sulfuric acid). The physical properties are identical to those of the product of Example 6.

We claim:

1. An aryl ether ketone of the formula

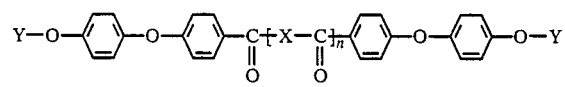

where
n is from 0 to 5,
X is

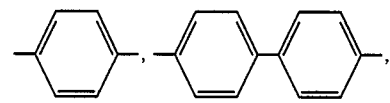

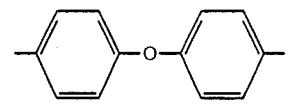

and
Y is tert-butyl, acetyl, benzyl, benzoyl or tert-butoxycarbonyl, or the same compounds bearing at least one ring-substituent selected from the group $C_1$–$C_8$-alkyl, $C_1$–$C_8$-alkoxy, aryl, chlorine and fluorine.

2. An aryl ether ketone of the formula

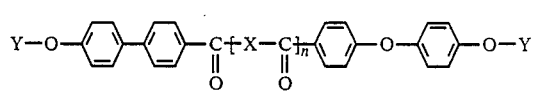

where
n is from 0 to 5,
X is

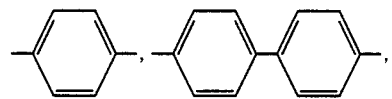

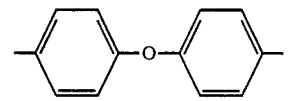

and
Y is H, or the same compounds bearing at least one ring-substituent selected from the groups $C_1$–$C_8$-alkyl, $C_1$–$C_8$-alkoxy, aryl, chlorine and fluorine.

3. An aryl ether ketone as claimed in claim 1 which is the compound 4,4'-Di(tert-butoxyphenoxy)benzophenone.

4. An aryl ether ketone as claimed in claim 1 which is the compound 1,4-Di(p-tert-butoxyphenoxybenzoyl)-benzene.

5. An aryl ether ketone as claimed in claim 1 which is the compound 4,4'-Di(p-tert-butoxyphenoxybenzoyl)-diphenyl.

6. An aryl ether ketone as claimed in claim 2 which is the compound 1,4-Di(p-hydroxyphenoxybenzoyl)benzene.

7. An aryl ether ketone as claimed in claim 2 which is the compound 4,4'-Di(p-hydroxyphenoxybenzoyl)-diphenyl.

* * * * *

UNITED STATES PATENT AND TRADEMARK OFFICE
CERTIFICATE OF CORRECTION

PATENT NO. : 4,835,242
DATED : May 30, 1989
INVENTOR(S) : EGGERSDORFER et al

It is certified that error appears in the above-identified patent and that said Letters Patent is hereby corrected as shown below:

In Claim 2, formula I requires an oxygen atom which must be inserted between the two benzene rings on the left end of the formula, exactly as shown in Claim 1.

Signed and Sealed this

Sixteenth Day of January, 1990

*Attest:*

JEFFREY M. SAMUELS

*Attesting Officer*     *Acting Commissioner of Patents and Trademarks*